United States Patent [19]

Duchesne

[11] Patent Number: 5,128,486
[45] Date of Patent: Jul. 7, 1992

[54] SULPHOLENES AND PROCESSES FOR THEIR PREPARATION AND USE

[75] Inventor: Jean-Pierre Duchesne, Lyons, France

[73] Assignee: Rhone-Poulenc Nutrition Animale, Commentry, France

[21] Appl. No.: 744,939

[22] Filed: Aug. 14, 1991

Related U.S. Application Data

[62] Division of Ser. No. 663,129, Mar. 4, 1991, Pat. No. 5,082,953.

[30] Foreign Application Priority Data

Mar. 5, 1990 [FR] France ................... 90 02724

[51] Int. Cl.$^5$ .......................... C07D 333/72
[52] U.S. Cl. .......................... 549/53; 549/49
[58] Field of Search .................. 549/53, 49

[56] References Cited

U.S. PATENT DOCUMENTS

| | | | |
|---|---|---|---|
| 2,624,664 | 1/1953 | Mowry et al. | 71/91 |
| 3,075,003 | 1/1963 | Blumenthal | 549/78 |
| 3,176,022 | 3/1965 | Blumenthal | 549/78 |
| 4,179,468 | 12/1979 | Kane et al. | 564/281 |
| 4,244,890 | 1/1981 | Kane et al. | 564/455 |

OTHER PUBLICATIONS

R. Bloch et al., Tetrahedron Letters, "A General and Steroselective Synthesis of (E, F)-Conjugated Diens", 24 (1), pp. 1247-1250 (1983).
N. Novitskoga et al., Chemical Abstracts, 88:190512f, "New Synthesis of 2-Thiahydrindon and Dicyclohexylsulfide", p. 734 (1978).
K. Takabe et al., Chemistry and Industry, "New Synthetic Routes to B-Cyclogeranyl Phenyl Sulphide", p. 540 (1980).
H. Pommer, Chemical Abstracts, 54:9799d, "2-(2,6,6-Trimethylcyclohex-1-en-Lyl)Acetaldehyde", abstract of DE 1,025,871 (1958).

Primary Examiner—Glennon H. Hollrah
Assistant Examiner—Mark W. Russell
Attorney, Agent, or Firm—Finnegan, Henderson, Farabow, Garrett and Dunner

[57] ABSTRACT

A sulpholene compound and more particularly 4,4-dimethyl-2,2-dioxo-1,2,4,5,6,7-hexahydro-benzo[c]thiophene. These compounds are prepared by bringing myrcene sulphone into contact with a strong acid. The compounds of the present invention can be used as synthesis intermediates in the preparation of vitamin A.

16 Claims, No Drawings

SULPHOLENES AND PROCESSES FOR THEIR PREPARATION AND USE

This is a division of application Ser. No. 07/633,129, filed Mar. 4, 1991 now U.S. Pat. No. 5,082,453.

The present invention relates to new sulpholene compounds and the process for preparing them. The present invention relates, more particularly, to the use of sulpholene compounds in the preparation of gamma- and delta-pyronenes, and the use of delta-pyronenes for the synthesis of vitamin A. It relates most particularly to three isomers of 4,4-dimethylhexahydrobenzothiophene 2,2-dioxide.

The sulpholenes of the present invention are preferably of the following general formula (I):

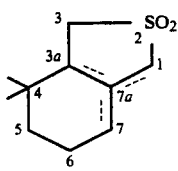

Formula (I)

wherein the broken line represents a single double bond which may be located at one of the 3a-7a, 1-7a or 7a-7 positions.

The three isomers of the present invention are as follows:
- 4,4-dimethyl-2,2-dioxo-1,3,4,5,6,7-hexahydrobenzo[c]thiophene,
- 4,4-dimethyl-2,2-dioxo-3,3a,4,5,6,7-hexahydrobenzo[c]thiophene, and
- 4,4-dimethyl-2,2-dioxo-1,3,3a,4,5,6-hexahydrobenzo[c]thiophene. Among these isomers, 4,4-dimethyl-2,2dioxo-1,3,4,5,6,7-hexahydrobenzo[c]thiophene (the β-isomer) is preferred.

Documents known in the prior art which describe derivatives of families of dioxothiophenes substituted in the 2-position of the thiophene ring by a terpene chain are U.S. Pat. No. 3,176,022 and U.S. Pat. No. 3,075,003. These documents describe the sulphonation of myrcene by sulphur dioxide followed by hydration in a sulphuric medium and decomposition under the action of heat, thus obtaining 2-methyl-6-methyleneoct-7-en-2-ol. These derivatives are used in the manufacture of perfume.

The primary prior art methods for the production of pyronenes are the dehydration of cyclogeraniol and the decomposition of β-cyclogeranyl-onium salts. These methods for the preparation of the gamma- and delta-pyronenes are described in U.S. Pat. No. 4,179,468 and U.S. Pat. No. 4,244,890.

The prior art fails to describe or suggest 2,2-dioxohexahydrobenzothiophene derivatives, which, according to the present invention, are synthesis intermediates useful in the production of vitamin A.

Compounds of the present invention having the general formula (I), may be prepared from 2,5-dihydro-3-(4-methyl-3-pentenyl)thiophene 1,1-dioxide (or myrcene sulphone) of formula (II)

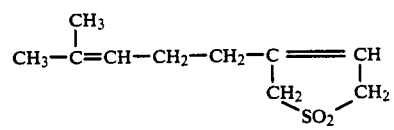

Formula (II)

by cyclization in the presence of a strong acid containing preferably less than 5% water. The strong acids are preferably selected from:
- sulphuric acid,
- alkyl-, aryl- or halogenosulphonic acids of the formula $RSO_3H$, more preferably:
  - methanesulphonic acid in which R is $CH_3$,
  - paratoluenesulphonic acid in which R is $CH_3-C_6H_4-$,
  - triflic acid in which R is $CF_3-$,
  - fluorosulphonic acid in which R is F—,
  - chlorosulphonic acid in which R is Cl—, and
  - sulphonic resins such as Amberlite 15,
- Nafion resins,
- perchloric acid, and
- heterogeneous acid catalysts, preferably:
  - silicas acidified by an acid treatment, for example, HF,
  - aluminas acidified by an acid treatment, for example, HF,
  - acid transition metal oxides,
  - zeolites, and
  - acidified clays.

The most preferable strong acid is sulphuric acid.

The acid may be used alone and may constitute both the reagent and the solvent, or it may be used in the presence of a separate solvent. The separate solvent is preferably inert under the reaction conditions and miscible with both the acid and the reaction products.

Inert solvents which may be used in the present invention include:
- halogenated solvents, preferably dichloromethane,
- carboxylic acids, preferably acetic acid, their esters, for example, ethyl acetate,
- nitro solvents, preferably nitromethane or nitrobenzene, and
- sulphones, preferably sulpholane.

In general, if a separate solvent is used, the rate of reaction is reduced and an increased amount of the α and γ isomers appear.

If the reaction is carried out in sulphuric acid, it is preferable to use a ratio, by volume, of strong acid to the sulphone compound of formula (II) which is preferably below 1:1 and more preferably ranging from 0.10:1 to 0.50:1.

If a sulphonic acid or a perchloric acid is used, it is preferable to use a molar ratio of sulphonic acid or perchloric acid to the sulphone compound of formula (II) ranging from 0.1:1 to 0.5:1.

The ratio chosen depends upon the acidity of the acid being used. The ratio may be adapted by those skilled in the art to provide the following characteristics:
- the desired optimum rate of reaction,
- the nature of the desired isomers, and
- the viscosity of the reaction mixture.

The preferred reaction conditions include a temperature preferably below 0° C. and still more preferably ranging from −10° C. to 0° C. The reaction time will be selected based upon the reaction conditions. The selection of the reaction conditions depends on the presence or absence of a solvent.

When using sulphuric acid, it is preferable to run the sulphone compound into the acid and to stop the reaction when all of the sulphone compound has been added.

Alternatively when using an acid diluted in an inert solvent, the contact between the sulphone compound of formula (II) and the strong acid may advantageously be prolonged beyond the time needed for complete addition of the strong acid into the solution of the sulphone compound.

The starting material used, which is a myrcene sulphone compound of formula (II), is prepared by bringing myrcene into contact with sulphur dioxide in the presence of a polymerization inhibitor at a temperature of between 60° and 100° C. This method of preparation is described in U.S. Pat. No. 3,176,022, at column 1, lines 50 to 60, which is specifically incorporated herein by reference.

The myrcene used in the preparation of the sulphone compound may be a pure product or a crude product. If it is a crude product it may contain, for example, terpene by-products from the synthesis, such as limonene.

The sulphone product may contain $\alpha$, $\beta$ and $\gamma$ sulphone. It is easy to isomerize the $\alpha$ and $\gamma$ sulphone into $\beta$-sulphone by warming the solution from minutes to hours at a temperature between about room temperature and 100° C. After the isomerization, the sulphones are essentially all $\beta$-sulphones.

The products of formula (I), which are the subject of the present invention, can be intermediates in the synthesis of vitamin A.

The compounds of the formula (I) can be easily converted to $\delta$-pyronene by heating at high temperature, and preferably in the presence of a basic catalyst. The following reaction using the $\beta$-sulphone of formula (I) as the starting material exemplifies this conversion:

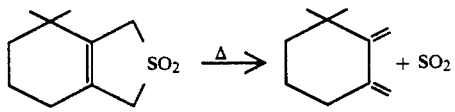

The basic catalyst is preferably selected from metal oxides, more preferably alumina, lime and magnesia, alkali hydroxides, carbonates and alcoholates, more preferably sodium methylate or potassium decanolate. The alcoholates can be produced in situ by contact between an alkali hydroxide and an alcohol.

The catalyst is preferably used in an amount of about 1 to 100% by weight relative to the sulpholene compound of formula (I). When the catalyst is an alcoholate, it is more preferably less than 10% and most preferably between about 1 and 10% based on a molar ratio to the compound of formula (I). If the catalyst used is based on an alkaline metal oxide or alkaline earth metal oxide, it is preferably 10 to 100% by weight, and more preferably about 100% by weight of catalyst relative to the amount of sulpholene compound present.

The reaction temperature is preferably higher than about 150° C. and more preferably ranges from about 250° C. to 300° C. when a catalyst is not used. When a catalyst is used, the temperature preferably ranges from about 150° to 250° C.

The reaction may be carried out in a continuous or discontinuous manner.

The $\delta$-pyronene obtained after cracking the compound of formula (I) can be easily purified by distillation.

$\delta$-pyronene can be used in the synthesis of cyclogeranyl intermediates which can be used in the synthesis of vitamin A and the carotenoids as described, for example, in German Patent No. 1,025,871 or in the article by K. TAKABE et al., Chem. and Ind. (1980), p. 540, the disclosures of which are specifically incorporated by reference.

$\delta$-pyronene may also be used as a synthesis intermediate in the manufacture of perfume to prepare $\alpha$-cyclogeraniol.

The following examples, given without any limitation being implied, enable the invention to be better understood without, however, limiting its scope.

EXAMPLE 1

98% $H_2SO_4$ (25 ml) was cooled to $-10°$ C., with vigorous stirring, in a 100 ml round-bottomed flask. 95% myrcene sulpholene (6.0 g; 28.5 mmol) obtained by the method of Example 1 of U.S. Pat. No. 3,075,003 was then run into the acid, over a period of about 10 min, keeping the temperature below 0° C.

The viscous brown solution was stirred for 10 min at 0° C. and then run slowly onto a water/ice mixture (100 g), with vigorous stirring.

The white solid which precipitated was filtered off, washed with water until neutral and then dried at 20° C. under 1 mmHg to give 5.9 g of the crude product.

After recrystallization from isopropyl ether (20 ml), $\delta$-pyronene sulpholene (Ia) (5.10 g; 25.5 mmols, yield=90%) was obtained in the form of white flakes. m.p. 90° C. Analysis by NMR spectrometry Sulpholene (Ia)

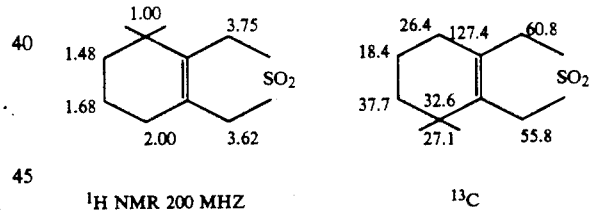

$^1$H NMR 200 MHZ     $^{13}$C

95% myrcene sulpholene (500 g; 2.375 mol) was dissolved in methylene chloride (100 ml) in a 2 liter round-bottomed flask fitted with a powerful mechanical stirrer, a dropping funnel and a thermometer. The temperature was maintained at about 0° C., and a solution of 98% methanesulphonic acid (121 g) in methylene chloride (100 ml) was run into the solution over a period of 2 hours.

After 15 min, the mixture was poured onto a mixture of water (500 ml) and ice (100 g) and extracted with methylene chloride (500 ml) and ethyl acetate (300 ml).

After evaporation of the solvents, a very thick brown oil (450 g) was obtained.

By crystallization from isopropyl ether (2 liters), a white solid (300 g) was obtained giving the following results by chromatography on silica:

sulpholene $I_a$ (240 g), m.p.=90° C.,
sulphone $I_b$ (20 g), m.p.=87° C., and
a mixture of sulphones $I_b$ and $I_c$ (20 g).

The structure of sulphones $I_b$ and $I_c$ was determined by NMR in $CHCl_3$ ref. HMD

¹H NMR 360 MHZ

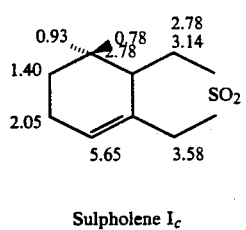

Sulpholene I$_c$

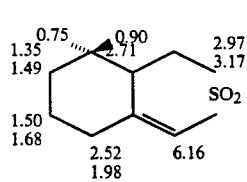

Sulpholene I$_b$

¹³C NMR 90 MHZ

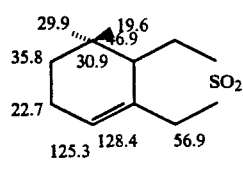

Sulpholene I$_c$

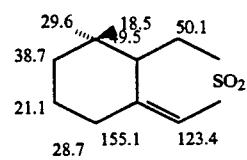

Sulpholene I$_b$

A posteriori analysis of the crude mixture enabled its composition by mass to be determined: 2.5% of hydrocarbons, 12.6% of myrcene sulpholene, 84% of cyclic sulphones I$_a$ 85% I$_b$ 10% I$_c$ 5% which is a degree of conversion =

$$\frac{\text{number of moles of product converted}}{\text{number of moles of solid material introduced}} = 85\%$$

The yield relative to the sulphone employed was approximately 72% for I$_a$, approximately 8.5 for I$_b$ and approximately 4.3% for I$_c$.

EXAMPLE 3 PYROLYSIS OF I$_a$

The following were charged into a 500 ml round-bottomed flask set up on a rotary evaporator:
cyclic sulpholene I$_a$ (40 g; 0.2 mol), and
neutral alumina of activity I (6 g).

The round-bottomed flask was rotated at about 200°–250° C. under a vacuum of 150 mmHg.

The distillate was condensed at 20° C. and collected in a round-bottomed flask at 0° C.

A colourless mobile liquid (19.5 g) consisting of:
δ-pyronene (17 g), and
sulpholene I$_a$ (2.5 g)
(by ¹H NMR analysis)
was obtained.

A flash distillation, b.p.=102° C./150 mmHg, of the crude product obtained pure δ-pyronene (15 g), analyzed by vapour phase chromatography; the yield was 55%.

EXAMPLE 4 PYROLYSIS OF I$_a$

The following were charged into a 100 ml round-bottomed flask set up on a rotary evaporator:
cyclic sulpholene I$_a$ (10 g; 0.05 mol), and
calcium oxide in powder form (10 g).

The round-bottomed flask was rotated at about 200°–220° C. under a vacuum of 40–50 mmHg. δ-pyronene (4.2 g), which was pure according to gas phase chromatography and NMR analysis, was trapped at −80° C. The yield was 62%.

EXAMPLE 5

The following were put into a 50 ml balloon flask that was surmounted by a condensor through which circulation of a cooling mixture was maintained at 0° C.:

5 g of sulpholene at 80° C. containing 15 mmoles in the form of I$_a$ and 5 mmoles in the form I$_c$.

48 g of ionol 104 mg of sodium methylate 12 ml of gilotherm ® (gilotherm is composed of 75% diphenylether and 25% diphenyl)

The mixture was heated for two hours at 60° C. under atmospheric pressure, and the disappearance of the I$_c$ isomer was confirmed.

Then using two refrigerated traps (dry ice and acetone), the mixture was placed under a vacuum of 200 mm of Hg. The mixture was gradually heated and maintained at a temperature between 160° and 186° C. while distilling the δ-pyronene that was formed.

The yield of pyronene in relation to the total sulpholene was 76.5%.

EXAMPLE 6

The following were put into the same apparatus as described in Example 5:

10 g of sulpholene (35 mmoles in the form I$_a$, 10 mmoles in the form Ic, and 5 mmoles in the form I$_b$).

5 g of ionol (0.5 mmole)

19.8 g (25 ml) of decanol 0.3 g of potassium hydroxide at 85% (5 mmoles).

The mixture was heated at 87° C. for 30 minutes under atmospheric pressue. The I$_c$ and I$_b$ isomers disappeared completely. The procedure then followed that explained in Example 5, above.

After an hour of distillation, the pyronene obtained was rectified in the presence of sodium bicarbonate.

The final yield of δ-pyronene in relation to the total sulpholene was 81%.

I claim:

1. A process for the preparation of a 4,4-dimethyl-2,2-dioxohexahydrobenzo[c]thiophene comprising the step of:
   contacting 2,5-dihydro-3-(4-methyl-3-pentenyl) thiophene 1,1-dioxide with a strong acid for a time sufficient to form said 4,4-dimethyl-2,2-dioxohexahydrobenzo thiophene.

2. The process according to claim 1, wherein the strong acid is an acid containing less than about 5% water.

3. The process according to claim 2, wherein the strong acid is an acid containing less than about 2% water.

4. The process according to claim 1, wherein the strong acid is selected from sulphuric acid, sulphonic acids, perchloric acid and heterogeneous acid catalysts.

5. The process according to claim 4, wherein the strong acid is sulphuric acid.

6. The process according to claim 4, wherein the sulphonic acids are selected from methanesulphonic acid, paratoluenesulphonic acid and sulphonic resins.

7. The process according to claim 2, wherein the strong acid is selected from sulphuric acid, sulphonic acids, perchloric acid and heterogeneous acid catalysts.

8. The process according to claim 7, wherein the strong acid is sulphuric acid.

9. The process according to claim 7, wherein the sulphonic acids are selected from methanesulphonic acid, paratoluenesulphonic acid and sulphonic resins.

10. The process according to claim 3, wherein the strong acid is selected from sulphuric acid, sulphonic acids, perchloric acid and heterogeneous acid catalysts.

11. The process according to claim 10, wherein the strong acid is sulphuric acid.

12. The process according to claim 10, wherein the sulphonic acids are selected from methanesulphonic acid, paratoluenesulphonic acid and sulphonic resins.

13. The process according to claim 1, wherein said contacting step is conducted in the presence of an inert solvent selected from halogenated solvents, carboxylic acids, esters of carboxylic acids, nitro solvents and sulpholane.

14. The process according to claim 13, wherein the solvent is dichloromethane.

15. The process according to claim 1, wherein the strong acid is sulfuric acid and wherein the ratio by volume of sulphuric acid to 2,5-dihydro-3-(4-methyl-3-pentenyl)thiophene 1,1-dioxide is below about 1:1.

16. The process according to claim 15, wherein the ratio by volume of sulphuric acid to 2,5-dihydro-3-(4-methyl-3-pentenyl)thiophere 1,1 dioxide ranges from about 0.10:1 to 0.50:1.

* * * * *

UNITED STATES PATENT AND TRADEMARK OFFICE
CERTIFICATE OF CORRECTION

PATENT NO. : 5,128,486

DATED : July 7, 1992

INVENTOR(S) : Jean-Pierre DUCHESNE

It is certified that error appears in the above-identified patent and that said Letters Patent is hereby corrected as shown below:

ON THE TITLE PAGE

In the Title, before "SULPHOLENES" insert --NEW--.

Claim 1, col. 6, lines 45 and 46, change
"4,4-dimethyl-2,2-dioxohexahydrobenzo thiophene" to
--4,4-dimethyl-2,2-dioxohexahydrobenzo[c]thiophene--.

Claim 16, col. 8, lines 10 and 11, change
"2,5-dihydro-3-(4-methyl-3-pentenyl)thiophere 1,1 dioxide" to
--2,5-dihydro-3-(4-methyl-3-pentenyl)thiophene 1,1-dioxide--.

Signed and Sealed this

Twenty-first Day of September, 1993

Attest:

BRUCE LEHMAN

Attesting Officer

Commissioner of Patents and Trademarks